United States Patent [19]

Hirschberg et al.

[11] Patent Number: 5,066,278
[45] Date of Patent: Nov. 19, 1991

[54] IMPLANTABLE INJECTION BODY

[75] Inventors: Jakub Hirschberg, Taeby; Bengt Svensson, Järfalla, both of Sweden

[73] Assignee: Siemens Aktiengesellschaft, Berlin and Munich, Fed. Rep. of Germany

[21] Appl. No.: 562,696

[22] Filed: Aug. 6, 1990

[30] Foreign Application Priority Data

Aug. 9, 1989 [EP] European Pat. Off. ........ 89114770.4

[51] Int. Cl.⁵ ............................................. A61M 5/14
[52] U.S. Cl. .................................. 604/256; 604/246; 604/263; 604/890.1; 604/265
[58] Field of Search ................ 604/51, 244, 246, 270, 604/890.1, 263-268, 256

[56] References Cited

U.S. PATENT DOCUMENTS

| 3,736,939 | 6/1973 | Taylor | 604/265 |
| 4,055,178 | 10/1977 | Harrigan | |
| 4,306,563 | 12/1981 | Iwatschenko | |
| 4,578,063 | 3/1986 | Inman et al. | 604/175 |
| 4,642,230 | 2/1987 | Whitehead et al. | 604/890.1 X |
| 4,643,712 | 2/1987 | Kulik et al. | 604/4 |
| 4,692,152 | 9/1987 | Emde | 604/164 |
| 4,936,835 | 6/1990 | Haaga | 604/265 |
| 4,976,703 | 12/1990 | Franetzki et al. | 604/247 |

FOREIGN PATENT DOCUMENTS

| 3115763 | 11/1982 | Fed. Rep. of Germany | |
| 3641107 | 6/1987 | Fed. Rep. of Germany | |
| 0048593 | 4/1976 | Japan | 604/265 |
| WO89/05671 | 6/1989 | PCT Int'l Appl. | |

Primary Examiner—John D. Yasko
Assistant Examiner—Adam J. Cermak
Attorney, Agent, or Firm—Hill, Van Santen, Steadman & Simpson

[57] ABSTRACT

An implantable injection body for the time-dependent dosable, long-term injection of a medication into a living being, the medication being stored in an implanted medication dosing device and being supplied by the latter to the injection body via a programmable pump arrangement. The injection body has a plurality of medication discharge openings, at least some of which are initially sealed, by a selectively openable seal, preferably by a dissolvable tissue-compatible, plastic material that dissolves at different times, so that, after closure of the initially unsealed discharge opening caused by overgrowth of connective tissue, agglomeration of matter, and/or the like, the initially sealed discharge openings can be selectively unsealed, preferably in serial fashion, to permit continued medication flow-through. Alternatively, the openable seals can comprise rupturable membranes of varying strengths.

26 Claims, 1 Drawing Sheet

5,066,278

IMPLANTABLE INJECTION BODY

BACKGROUND OF THE INVENTION

The invention generally relates to an implantable injection body for time-dependent, dosable, long-term injection of a medication into a living being. More specifically, the invention relates to an implantable injection body wherein medication to be long-term, time-dependent, dosably injected into a living being is stored in an implantable medication dosing device and is supplied to the injection body via a programmable pump arrangement, the injection body being provided with a plurality of medication discharge openings that follow one another in the flow direction of the medication and that are arranged in spaced apart construction.

In many instances, liquid medications must be supplied to a living being over a relatively long period of time. Medication dosing devices are currently available for such long-term applications, for example, as required in the case of diabetics. These devices administer a liquid medication, for example, insulin, to the patient in programmable doses and at programmable intervals.

External and/or implantable micro-dosing devices can be involved. In either instance, the medication is delivered to the patient via an implantable injection body. This delivery can occur in various ways, namely subcutaneously, intraperitoneally, or intravenously.

In the case of subcutaneous delivery, a catheter hose is subcutaneously laid between the discharge of the medication pump and the injection location, the distal end of this catheter hose being constructed as an injection needle made of metal or plastic. In the case of intravenous injection, the distal end of the catheter can be a blunt end or can comprise a specific tip that is provided with a discharge opening for the medication. An implantable injection body in catheter form is disclosed in West German patent application DE-A-38 05 508/2, having corresponding European patent 330012 and U.S. patent application Ser. No. 310,617, filed Feb. 15, 1985, now U.S. Pat. No. 4,976,703, the teachings of which are fully incorporated herein by reference.

As a consequence of reactions of the body of the living being to foreign bodies, such injection bodies are attacked within defined time spans. Generally, a connective tissue agglomerates to the injection body beginning from the distal end and continuing backwards. Over and above this, body cells, macro-molecules and tissue particles can penetrate into the medication discharge openings and can agglomerate to the inside walls of the injection body. The discharge opening is ultimately closed due to these body reactions of the living being.

In order to delay this process, the catheter construction of DE-A-38 05 508/2 is provided with a discharge opening that is constructed displaced from the tip in the distal direction. In this construction, moreover, through slots that serve as emergency openings can be distally provided in displaced relation from the main discharge opening, these emergency openings spreading under the pressure of the medication when the main discharge opening is blocked. Plastic material can be employed to make the catheter, thus enabling an emergency discharge. Since the adhesion of growths is particularly dependent on the surface roughness of the injection body and on the surface design thereof, such injection bodies have been coated with especially smooth, tissue-compatible protective layers and the geometrical shape of the injection body has been selected such that corners and edges are avoided.

All of these measures are in fact suitable for retarding the medication discharge opening from closure from being grown shut or blocked, but cannot prevent such closure. The bypass of the medication discharge to emergency openings also does not necessarily lead to a malfunction-free continuation of the injection process, but at most prevents an immediate interruption of the medication delivery. Due to the higher liquid pressure in the overall medication line, as a consequence of the force needed to supply the medication from the closed or closing slot-shaped emergency openings, the energy consumption of the pump is increased. This increased pump energy consumption can lead to a shortening of the useful life of the energy source.

Over and above the foregoing, the slots of the emergency discharge openings have relatively sharp edges. The sharp edges in turn can lead to an accelerated agglomeration of tissue particles and, thus, to a relatively short service life of the openings.

The provision of a plurality of simultaneously functioning openings also is disadvantageous because the throughput rate of the medication with reference to every individual opening decreases in accordance with the number of openings. As experience has taught, the service life of an opening is roughly proportional to the throughput rate of the medication. The service life of such an opening is thus greater the higher the through-put rate. This results in contradictory design considerations: the desire to reduce the number of openings to increase the throughput rates per opening, and the desire to increase the number of openings to provide for more bypass openings. At any rate, it has not been possible to achieve services lives for known catheters for the injection of medications that even approximate the useful life of the dosing device.

SUMMARY OF THE INVENTION

The invention provides for extended service life of an implantable injection body such that it is at least equal to the functional duration of an implanted dosing device.

To this end, the invention provides in an embodiment an implantable injection body for long-term time dependent injection of a medication into a living body, the medication being stored in an implantable dosing device and operatively supplied to the injection body via a suitable pump arrangement, comprising two or more discharge openings in the injection body through which the medication is supplied into the living body, and a dissolvable tissue-compatible seal material operatively initially sealing all of the discharge openings except one so that when the initially unsealed discharge opening becomes closed due to tissue overgrowth or coagulation and the like, another discharge opening becomes unsealed to allow continued supply of the medication.

What is thereby achieved is that a plurality of openings can be available for the medication discharge, one at a time. Preferably, a further opening is used only after the blockage of a previously used opening. By enabling use of only one further opening, the flow-through rate per opening of the medication remains roughly the same. Further, many openings can be provided so that the service life of the injection body can be nearly arbitrarily extended. As a result, repeated surgical operations to replace the injection body that previously were necessary, even given a functioning medication dosing device, are superfluous.

In one embodiment of the invention, each discharge opening is sealed by a different thickness of seal material. What is thereby achieved is that the durabilities of the seals of the respective discharge openings are predetermined by the differing thicknesses of the seal material.

In one embodiment of the invention, the seal material dissolves under biochemical influences.

In another embodiment, the seal material dissolving can be triggered by an external influence, for example, ultrasound influence.

In one embodiment, the injection body is provided with a paracentisis septum that is accessible from outside of the living being so that a rinsing agent can be injected under a pressure sufficient to selectively unseal a sealed opening. Thus, the external influence can be provided in the form of an elevated exertion of pressure independently of the normal medication delivery, for example, with the rinsing agent injected into the septum, the seals being operative to unseal at different pressures.

In a further embodiment of the invention, wherein the injection body is a catheter, the catheter itself has a length dependent on the 3-dimensional expanse of the injection region composed of biochemically dissolvable material, so that, beginning from the catheter tip, the material dissolves opposite the flow direction of the medication before a connective tissue growth reaches such a degree that the catheter tip is blocked. Instead, the catheter tip continuously avoids being possibly grown shut as the seal material dissolves to unseal openings thereunder.

Further features and aspects of the invention are set forth in greater detail in the detailed description of the presently preferred embodiments and accompanying drawings.

DETAILED DESCRIPTION OF THE PRESENTLY PREFERRED EMBODIMENTS

Figure 1:
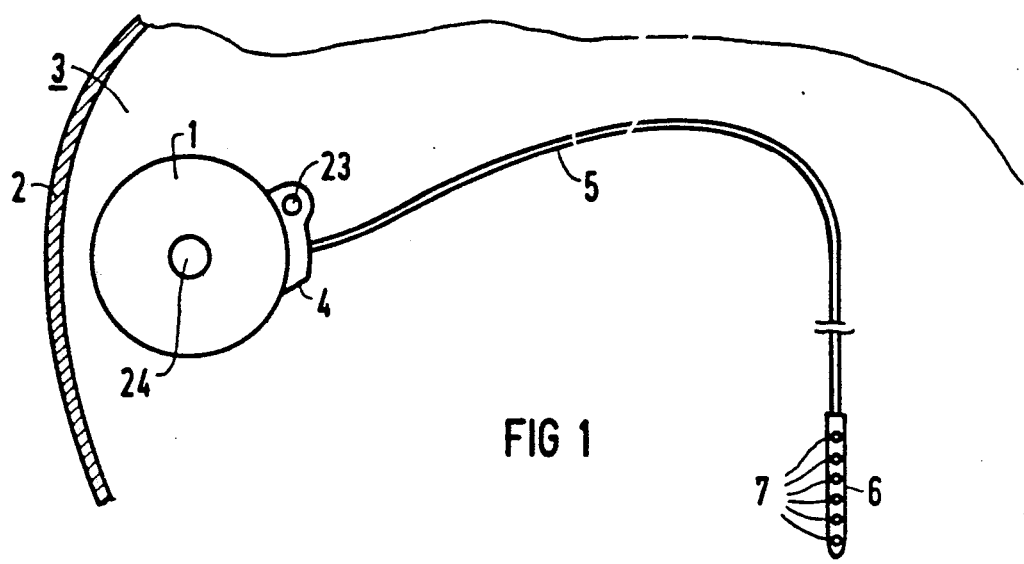
FIG. 1 illustrates an implantable medication dosing device having a catheter hose connected to the output thereof and having a catheter tip arranged at its discharge end.

In FIG. 1 there is illustrated an implantable medication dosing device 1 that is introduced under the skin 2 in the stomach area 3 of a patient. At its medication exit, the medication dosing device 1 has a catheter connector 4 that connects a catheter 5 to a pump (not shown) of the medication dosing device 1.

The catheter 5 that, for example, can be introduced into a large vein, has its discharge side provided with a medication discharge cannula 6 that has a plurality of medication discharge openings 7 that follow one another in flow direction of the medication. The cannula 6 and/or catheter 5 serves as an injection body.

As discussed above, the body of the patient reacts to the catheter 5 as a foreign body and attempts to cover the catheter 5 with connective tissue, so that the medication discharge opening becomes blocked. Such a blockage can also occur in that foreign particles or medication that crystalizes agglomerate to the opening to thereby plug it. Given an intravenously positioned catheter, such a blockage can also occur due to coagulation of blood.

Normally, when the discharge openings become blocked or overgrown by connective tissue, surgical intervention must be performed and the catheter must be replaced. This is an operation that is burdensome for the patient that, in many instances, is required far before the end of the functional life of the implanted medication dosing device, for instance when the end of the useful battery life is reached. This is especially true, for example, in the case of a battery rechargeable by wireless energy transformation, where one can obtain an even longer useful life of the medication dosing device. Thus, the intervals of the surgical interventions for replacing the implanted body essentially are defined by the duration that the discharge opening of the medication discharge cannula 6 remain unsealed or unblocked.

When, as illustrated in FIG. 1, the cannula 6 is provided with a plurality of medication discharge openings 7 that follow one another in the flow direction of the medication and that are arranged at spatial distances from one another, the flow rate of the medication with respect to every individual opening would normally be extremely low. Since the speed with which every individual opening grows shut is also dependent on the throughput rate of the medication, the rate of closure of every individual medication discharge opening is increased, as also discussed above, so that the advantage initially present due to the presence of a plurality of openings is in turn greatly diminished.

Figure 2:
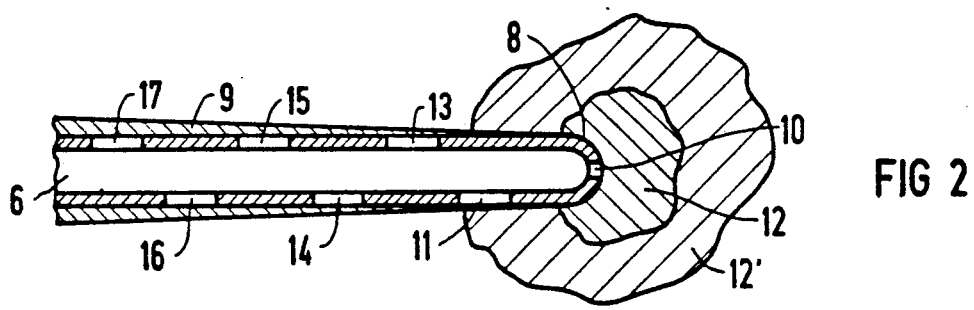
FIG. 2 illustrates a catheter tip having a plurality of medication discharge openings and an envelope that seals them.

In FIG. 2, it is illustrated how this disadvantage of a reduced flow rate of the medication can be avoided given a great plurality of openings. To this end, all discharge openings except for a single discharge opening are initially closed or sealed by a coating of seal material 9. Only a primary medication discharge opening 10 in the tip 8 of the cannula 6 is initially left open or unsealed.

A biologically compatible polyester that corresponds to that employed, for example, for self-dissolving suture surgical material can be used as the seal material 9. It is also possible to employ a bio gel, for example hydroxy butyrate or hydroxy venenate, as the seal material 9.

A connective tissue 12 growing-over process begins some time after the implantation of the catheter 5. The dissolving process of the seal material 9, however, begins immediately and continuously. Thus, in a preferred embodiment, as illustrated in FIG. 2, the seal material 9 is not imparted with a constant wall thickness, but with a wall thickness that continuously thickens or increases opposite the flow direction of the medication. As a result, the serially arranged sealed discharge openings 11, and 13-17 will be exposed in serial fashion commencing with the opening 11 lying closest to the primary medication discharge opening 10. Preferably, this occurs exactly at that point in time in the ideal case at which the primary discharge opening 10 closes due to the growth 12.

Due to the increasing wall thickness of the seal material 9 in the direction opposite the medication flow, this process will successively continue at the following, sealed discharge openings 13-17. When, thus the growth has achieved the expanse identified 12', the discharge opening 11 becomes closed but the discharge opening 13 will have become unsealed. This event is repeated in ascending succession until, ultimately, the last sealed discharge opening 17 no longer functions, i.e. is grown closed. Depending on the spatial extent of the injection region available, the number of sealed medication discharge openings can be selected such that the time elapsing until the last opening in the flow direction of the medication grows shut roughly corresponds to the service life of the medication dosing device 1.

The rate of growth of the connective tissue 12 and, thus, the intervals between the closures of the individual medication openings 10, 11, and 13-17 for an individual living being is a quantity that can deviate greatly from the statistical average. It can therefore be expedient to influence the enabling or unsealing of sealed discharge openings by an external influence. Such an external influencing, for example, can ensue with the assistance of a focused ultrasound beam acting on the opening to be respectively opened after imaging localization.

Figure 3:
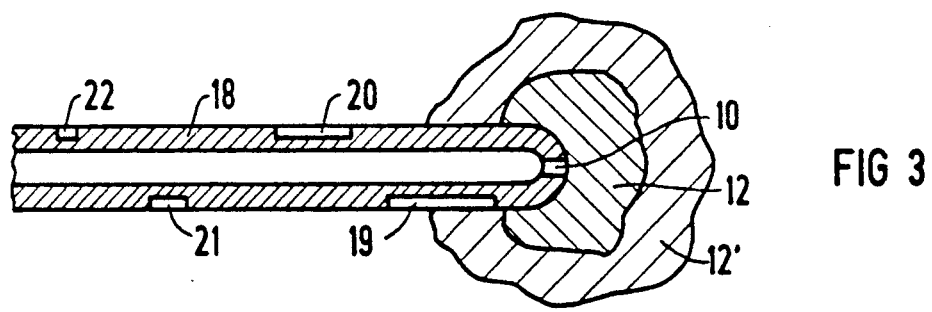
FIG. 3 illustrates another embodiment of a catheter tip having a plurality of medication discharge openings with different diameters.

To this end, in FIG. 3 there is illustrated another solution for influencing unsealing of a sealed discharge opening. As illustrated, a medication discharging cannula 18 is provided with recesses 19-22 of different diameters in the outside wall thereof. The recesses eventually serve as medication discharge openings but initially do not extend through the wall of cannula 18. The remaining, residual material that first closes the openings is a membrane with a preselected thickness.

The initially closed discharge opening 19 lying closest to the primary, opened discharge opening 10 (proceeding opposite the flow direction of the medication) has a larger diameter relative to the primary discharge opening 10. Proceeding against the direction of flow of the medication, the diameters of the remaining discharge openings 20-22 decrease by specific increments. Thus, the opening 22 furthest from the opening 10 has the smallest diameter while opening 19 has the largest diameter.

The unsealing of the openings can proceed such that, when, for example, the primary discharge opening 10 grows shut, the residual membrane of the discharge opening 19 is opened by the rising liquid pressure of the medication, the opening 19 being opened first because of its larger diameter which translates into a weaker membrane that will rupture before those membranes of the other discharge openings in view of the increased internal pressure.

With reference also to FIG. 1, a rinsing septum 23 can be allocated to the catheter connecting piece 4, so that rinsing fluid can be injected into the septum 23 from outside the body of the living being, via a valve arrangement (not shown). The septum 23 preferably is blocked from the medication reservoir (not shown) that is refillable via a medication refilling septum 24, but is open relative to the catheter 5, for example, via a check valve arrangement. The catheter pressure can thus be increased via injection of a rinsing agent to an extent such that, when a medication opening grows shut, the membrane of the next opening to be forced open to become transmissive.

The initially closed discharge openings 19-22 can also be through-bored and can be initially closed by the seal material. In this case, the thickness of the material of the seal material again must increase with decreasing diameters of the medication discharge openings. The absolute material thickness of the seal material must be selected such that the discharge openings are not prematurely unsealed.

Figure 4:
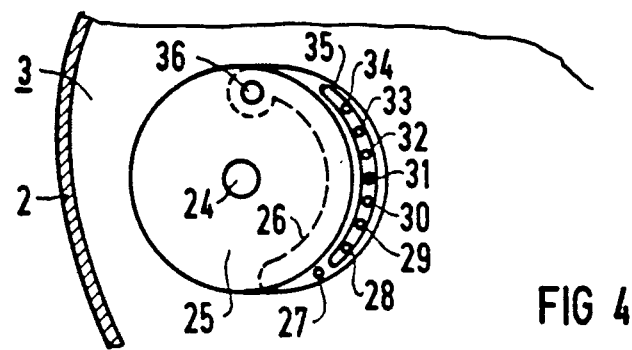
FIG. 4 illustrates a medication dosing device for direct discharge of the medication via a plurality of discharge openings sealed in a time-dependent manner that are arranged in a row in the generated surface of the dosing device.

In FIG. 4, there is illustrated another medication dosing device 25 implanted in the stomach area 3 of a patient, wherein the injection body is a component part of the dosing device itself. The dosing device is equipped with a peripheral medication discharge chamber 26 (only indicated by way of suggestion) that is internally connected to the output of the dosing pump (not shown) and that communicates with the outside of the dosing device via a series of medication discharge openings 27-34 through the wall of the dosing device. Only the discharge opening 27 is initially open, whereas the discharge openings 28-34 are initially covered with an appropriate dissolvable seal material 35.

Beginning from the discharge opening 28 up to the discharge opening 34, the seal material 35 can have a steadily increasing thickness in a fashion similar to the seal material 9 of the medication discharge cannula of FIG. 2; however, analogous to the medication discharge cannula of FIG. 3, the hole diameter of the discharge openings can be selected so as to be continuously decreasing beginning with the relatively large diameter of the opening 28 to the relatively small diameter of the opening 34. Also, in a manner similar to that illustrated in FIG. 3, the discharge openings 28-34 can be closed with a seal material that, beginning with the discharge opening 28, can likewise continuously increase in thickness up to the discharge opening 34, so that, given a material disintegration or dissolving ensuing on the basis of biochemical influences, the discharge openings can be successively made available for the passage of medication. The final unsealing can ensue under the pressure of a rinsing agent with the assistance of a further rinsing septum 36 that discharges into the medication discharge chamber 26.

While a preferred embodiment has been shown, modifications and changes may become apparent to those skilled in the art which shall fall within the spirit and scope of the invention. It is intended that such modifications and changes be covered by the attached claims.

We claim:

1. An implantable injection body for long-term time dependent injection of a medication into a living being, the medication being stored in an implantable dosing device and operatively supplied to the injection body via a suitable pump arrangement, comprising:
    two or more discharge openings in said injection body through which the medication is supplied into said living body; and
    a dissolvable tissue-compatible seal material operatively initially sealing at least some of said discharge openings such that as said seal material dissolves, these initially sealed discharge openings become unsealed at different times.

2. The injection body of claim 1, wherein the discharge openings are positioned serially along a flow direction of the medication through the injection body.

3. The injection body of claim 2, wherein the discharge openings are positioned on opposite sides of the medication flow in two rows, one row of discharge openings being arranged in offset position relative to the other row of discharge openings.

4. The injection body of claim 1, wherein the injection body comprises an injection cannula operatively connected at a distal end of a catheter.

5. The injection body of claim 4, wherein one discharge opening is initially unsealed and is positioned at a distal end of the cannula.

6. The injection body of claim 1, wherein the injection body comprises an integral component of the dosing device such that said discharge openings comprise openings that extend through a housing of the dosing device.

7. The injection body of claim 1, wherein said seal material comprises a plastic synthetic.

8. The injection body of claim 7, wherein said seal material comprises a synthetic that dissolves due to biological influences within a time span defined by a thickness of a layer of the synthetic.

9. The injection body of claim 7, wherein said seal material comprises a synthetic that dissolves under a noninvasive influence such as a thermal or chemical influence.

10. The injection body of claim 1, wherein at least two of said initially sealed discharge openings are sealed by different thicknesses of said seal material.

11. The injection body of claim 1, wherein said injection body is provided with a paracentesis septum that is accessible from outside of said living being and into which a rinsing agent can be injected under a pressure sufficient to cause a sealed discharge opening to become unsealed.

12. The injection body of claim 1, wherein said discharge openings have different diameters.

13. The injection body of claim 1, wherein said injection body comprises a catheter that is coated by said seal material in tapered fashion such that a thickness of said seal material increases from a distal end of said catheter to a predetermined point along said catheter.

14. An injection body through which medication is discharged into a living being comprising a plurality of medication discharge openings through which the medication is supplied into the living being and a dissolvable, tissue compatible material operatively covering said body so that initially at least some of said discharge openings are sealed closed so that over time, said initially sealed discharge openings become unsealed at different times due to dissolving of said seal material to permit transmission of the medication therethrough.

15. The injection body of claim 14, wherein the seal material comprises a synthetic plastic.

16. The injection body of claim 14, wherein said initially sealed discharge openings are arranged serially along a flow direction of the medication.

17. The injection body of claim 14, wherein said seal material is applied in varying thicknesses to said discharge openings so that said discharge openings become unsealed at different points in time over the life of the injection body.

18. The implantable injection body of claim 14, wherein said seal material comprises a biogel.

19. The implantable injection body of claim 14, wherein said seal material comprises hydroxy butyrate.

20. The implantable injection body of claim 14, wherein said seal material comprises hydroxy venemate.

21. An implantable injection body operatively associated with a medication dosing device for long-term, time dependent discharge injection of medication into a living being, the medication being stored in the medication dosing device and being supplied to the injection body via a pump, the injection body comprising:
 a distal end from which said medication is supplied to said living body;
 a plurality of medication discharge openings in said distal end; and
 a dissoluble tissue compatible seal material covering said body so as to initially seal all of said discharge openings except one.

22. A body through which a fluid is transmitted comprising a plurality of discharge openings in a wall of said body and a dissolvable seal material initially sealing at least some of said discharge openings, said initially sealed discharge openings being operative to become unsealed at different times over time as said seal material dissolves.

23. The body of claim 22, wherein said seal material is applied in different quantities to said discharge openings so that said initially sealed discharge openings are operative to become unsealed at different times.

24. An injection body for injecting medication into a living being, comprising a plurality of discharge openings in said body, at least some of said discharge openings initially being sealed by selectively openable seals, so that as an unsealed discharge opening becomes overgrown by connective tissue or plugged by agglomerated matter, said initially sealed openings can be selectively unsealed to permit continued injection of medication into said living being.

25. The injection body of claim 24, wherein said seals comprise thin membrane walls that can be selectively ruptured due to a pressure differential between an interior of said injection body and an exterior of said injection body.

26. The injection body of claim 24, wherein said seals comprise dissolvable tissue compatible material, a quantity of which determines when a particular discharge opening becomes unsealed.

* * * * *